(12) United States Patent
Gerhard et al.

(10) Patent No.: US 6,970,238 B2
(45) Date of Patent: Nov. 29, 2005

(54) SYSTEM FOR INSPECTING THE SURFACES OF OBJECTS

(75) Inventors: Detlef Gerhard, Munich (DE); Johannes Lechner, Munich (DE)

(73) Assignee: ICOS Vision Systems NV, Heverlee (BE)

( * ) Notice: Subject to any disclaimer, the term of this patent is extended or adjusted under 35 U.S.C. 154(b) by 0 days.

(21) Appl. No.: 10/258,141

(22) PCT Filed: Apr. 12, 2001

(86) PCT No.: PCT/DE01/01442

§ 371 (c)(1),
(2), (4) Date: Mar. 11, 2003

(87) PCT Pub. No.: WO01/79822

PCT Pub. Date: Oct. 25, 2001

(65) Prior Publication Data

US 2003/0160953 A1 Aug. 28, 2003

(30) Foreign Application Priority Data

Apr. 19, 2000 (DE) .................. 100 19 486

(51) Int. Cl.⁷ .............................. G01N 21/00
(52) U.S. Cl. .................. 356/237.4; 356/237.2
(58) Field of Search .............. 356/237.1–237.5; 382/8, 22, 27, 28; 250/208.1, 226, 559.07, 559.08, 559.4, 559.41, 559.44, 559.45, 559.46

(56) References Cited

U.S. PATENT DOCUMENTS 4,314,763 A   2/1982  Steigmeier et al.
4,555,798 A * 11/1985  Broadbent et al. .......... 382/144
6,166,393 A * 12/2000  Paul et al. .............. 250/559.08
6,198,529 B1 *  3/2001  Clark et al. .............. 356/237.5
6,373,565 B1 *  4/2002  Kafka et al. .............. 356/237.4
6,407,809 B1 *  6/2002  Finarov et al. ........... 356/237.3
6,587,193 B1 *  7/2003  Reinhron et al. ......... 356/237.5
6,636,302 B2 * 10/2003  Nikoonahad et al. ..... 356/237.2

FOREIGN PATENT DOCUMENTS

DE    35 34019 C2    4/1987
DE    44 22 861 C2   1/1996
DE    19734074 C2    2/1998
EP    0 335 559 A2   10/1989
EP    0 385 625 A2   9/1990
EP    0 557 558 A1   9/1993
EP    0 677 739 A1   10/1995
EP    0 696 733 A1   2/1996

OTHER PUBLICATIONS

Patent Abstract of Japan, Publication No. 07209199, Publication Date Aug. 11, 1995.
Patent Abstract of Japan, Publication No. 04198846, Publication Date Jul. 20, 1992.
Patent Abstract of Japan, Publication No. 11064232, Publication Date Mar. 5, 1999.

* cited by examiner

*Primary Examiner*—Michael P. Stafira
(74) *Attorney, Agent, or Firm*—Staas & Halsey LLP

(57) ABSTRACT

An inspection system optically examines the surfaces of objects to detect surface errors. The system scans image strips and, consequently, a given surface rapidly and with sufficient resolution using a linescan camera and an upstream microscope by aligning the captured lines.

20 Claims, 1 Drawing Sheet

SYSTEM FOR INSPECTING THE SURFACES OF OBJECTS

CROSS REFERENCE TO RELATED APPLICATIONS

This application is based on and hereby claims priority to PCT Application No. PCT/DE01/01442 filed on 12 Apr. 2001 and German Application No. 100 19 486.9 filed on 19 Apr. 2000, the contents of which are hereby incorporated by reference.

BACKGROUND OF THE INVENTION

The invention relates to a system and a method for optically testing surfaces for defects contained therein.

Quality control plays an important role in the automatic fabrication of industrial parts, in particular of semiconductor products and, in particular, explained using the example of a semiconductor wafer. The surface of a wafer should be free from conchoidal fractures after a sawing process, and be free from particles, and linking units such as fuses should be intact. Devices or methods that can be integrated into the organization of the fabrication should be applied in the appropriate testing of the surface in order to detect defects.

Depending on the size of a test object, and depending on the required resolution, a manual visual inspection with the aid of obliquely incident light and of a test object that executes wobbling movements can, for example, take place between individual method steps in the fabrication. Furthermore, an automatic inspection can be performed with the aid of a line scan camera by scanning once over the entire object. The number of pixels in the line and the width of the image dictate the pixel resolution per line unit. This is typically 40 $\mu$m.

Automatic inspection in the case of a conventional scanning operation is also known. Here, the surface of the test object is scanned with the aid of a two-dimensionally resolving camera. Variations in the illumination permit resolutions at different levels. Inspection with the aid of laser scanning on the basis of different principles is a further method from the related art. In this case, the laser beam mostly scans the object, object and laser beam moving at high speed relative to one another.

The method from the related art that is most promising for the automatic inspection of wafer surfaces is automatic inspection with the aid of a two-dimensionally resolving camera. However, manual visual inspection also continues to be applied.

SUMMARY OF THE INVENTION

It is one possible object of the invention to make available a sufficiently fast and reliable system for the fabrication, and a method for testing surfaces on test objects, it being possible at the same time to achieve a sufficiently high resolution.

One aspect of the invention is based on the finding that it is possible to inspect surfaces of a test object by using a system in a measuring head comprising a one-dimensionally resolving line scan camera, an optical system and a lighting unit in conjunction with a highly resolving positioning system, the positioning system moving the test object relative to the measuring head with the line scan camera. It is particularly provided in that case that the camera, which produces an image strip stepwise or continuously, is moved over the entire surface of the test object or of the prescribed regions thereof. The image line or the individual pixels of the image line can be read out serially or in parallel. To inspect the surface of the test object, the measuring head and test object are moved relative to one another in a meandering fashion so to give the selected surface is completely scanned. The image strips thus produced are evaluated online (in real time), or assembled to form an overall image and evaluated subsequently.

It is particularly advantageous to use a microscope as the optical system. In conventional illumination, this permits defects to be found in the surface of an object to be represented with better resolution.

A measuring head or a line scan camera with an objective or a microscope is moved relative to the surface of an object in order to fully examine a surface of the latter. This is performed by the lateral movement of an object that is fastened on a positioning system. With regard to the resolution, required for the inspection, on the image side is fulfilled by this positioning system via an appropriately fine rastering or determination of position in the lateral movement of the object. A relative path of movement between the line scan camera and object can preferably be meandering, spiral or circular. The spiral or circular relative movement is best suited to circular wafers. For the purpose of evaluating the overall object scene, the image strips detected sequentially and picked up by the line scan camera are parts of an overall image that is assembled in an evaluation unit. The evaluation of this image with regard to surface defects that occur can be performed simultaneously or later with the aid of prescribed categorization features.

It is advantageous to have different types of illumination with regard to light field, dark field, or else transmitted light in order to manipulate surfaces reflecting in different ways, in particular specula surfaces.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
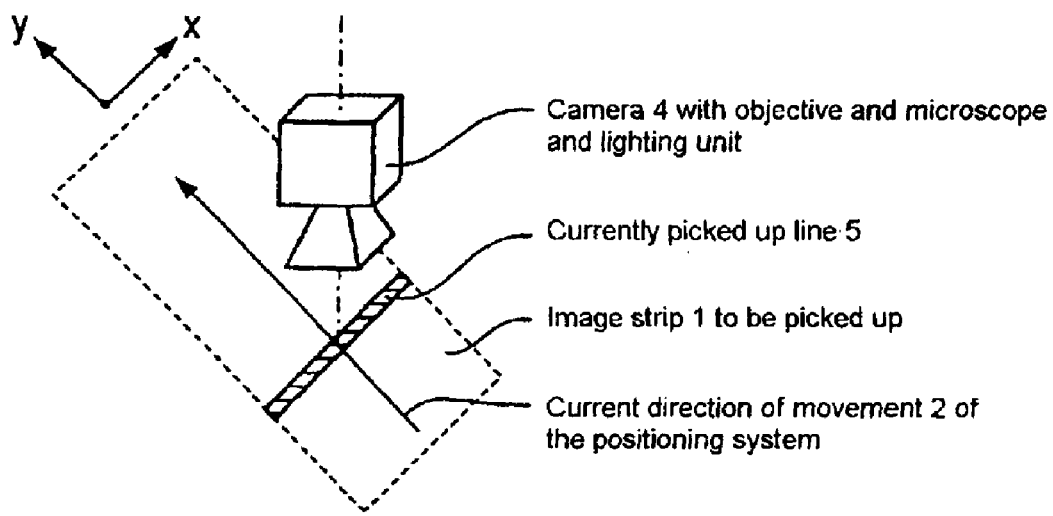
FIG. 1 shows a line scan camera that sequentially picks up a multiplicity of lines 5 on the object surface in the direction of movement 2 relative to the image strips 1 to be picked up overall.

Reference will now be made in detail to the preferred embodiments of the present invention, examples of which are illustrated in the accompanying drawings, wherein like reference numerals refer to like elements throughout.

A substantial advantage in the use of a line scan camera for inspecting object surfaces resides in simplified illumination. In addition, it is possible in conjunction with the same resolution to analyze larger samples than in the case of using a two-dimensionally resolving camera. Larger strip widths are therefore available in order to accomplish an analysis of the surface of an object. For example, a segment with 1000×1000 pixels in conjunction with 8 k pixels× resolution per pixel is a possibility using a two-dimensionally resolving camera. In the case of a one-dimensionally resolving line scan camera that is moved transversely to the longitudinal extent of the line in conjunction with a highly resolving positioning system for an object, a resolution of 1 $\mu$m is possible, when a line with 8000 (8 k) pixels, for example, is used and the relative movement between the object and camera is 10 mm/sec. A further advantage relates to the continuous imaging. By contrast therewith, a two-dimensional camera requires a plurality of individual images overlapping in the edge region for the purpose of mutual orientation.

The system and method can be used, in particular, for all types of optical inspection on wafer surfaces.

Figure 3:
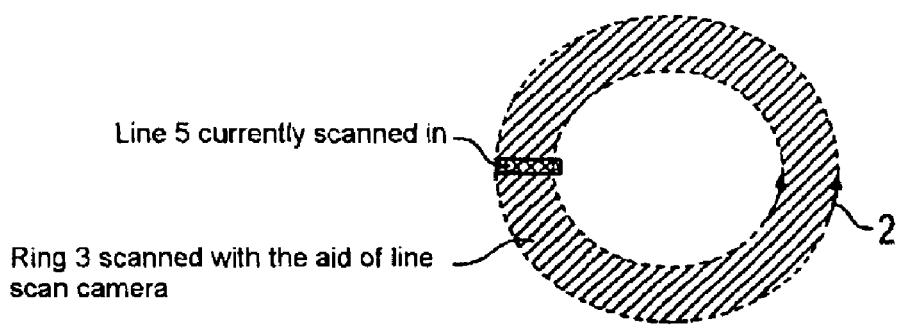
FIG. 3 shows a currently picked up line 5 that sweeps over a ring on an object surface by being picked up sequentially.

Use is made of a one-dimensionally resolving line scan camera having, for example, 4000 or 8000 pixels, a highly accurate positioning table, which can be positioned or sets an object position, a lighting unit, an optical system, in particular a microscope, that is positioned between the camera and object, and an image processor for storing the data picked up and for analyzing these image data. The analysis of the image data can be performed simultaneously (real time) or subsequently. FIG. 1 shows how the surface to be inspected is picked up with the aid of the line scan camera 4 in a meandering fashion corresponding to the prescribed direction of movement 2. This can also be performed in circular fashion in accordance with FIG. 3, movement being performed over a plurality of circles of different radii. The object is moved precisely under the line scan camera with the aid of a positioning device during the scanning operation.

FIG. 1 shows that the camera 4 has a microscope, for example, arranged upstream and is currently picking up a line 5, and that an image strip 1 is picked up by aligning a multiplicity of lines 5 stepwise or continuously. In this case, the length of a line 5 (longitudinal extent) extends in the x-direction, and the width of a line 5 extends in the y-direction (0 direction of movement). An image strip 1 is therefore reduced overall by aligning the lines 5.

Figure 2:
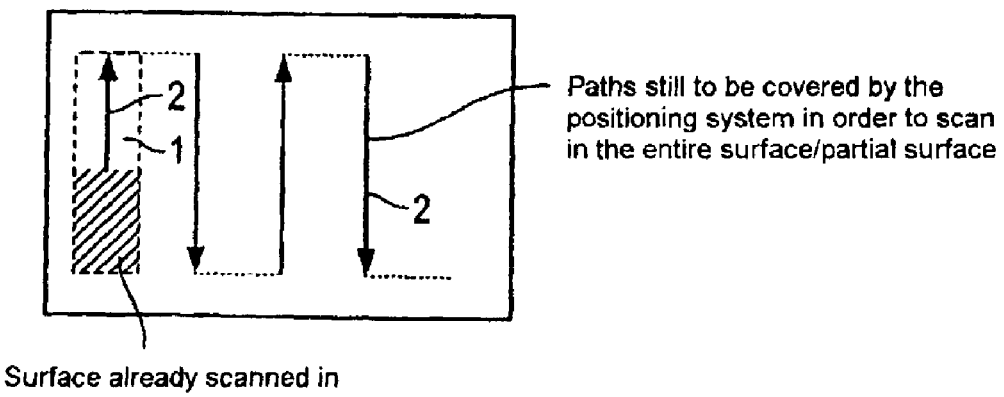
FIG. 2 shows the structure of the overall image that is produced by meandering movement over the object surface in accordance with FIG. 1, and subsequent assembly of the image strips to form an overall image.

FIG. 2 shows a surface that has already been scanned in at the start of the pick-up operation. The image strip 1 that is to be detected has been defined previously. The path of movement, that is to say the direction of movement 2, in which the image strips 1 are picked up is likewise fixed. The overall predetermined surface of an object can be detected thereby.

During a scanning operation, the image strip position of the start of the strip is linked to the position of the positioning system. A mutual relative assignment of the image strips 1 is detected thereby. A further application provides that only half of a wafer is scanned in, and the wafer support (chuck), on which the wafer rests, is rotated by 180° before a second scanning operation. The entire wafer is thereby scanned overall with the aid of single-axis positioning.

Illumination of the object surface can be a permanent illumination, but it is also possible to use flashes for specific requirements. The object is generally set rotating in order to constitute circular or annular scanning. The decision as to which type of illumination, bright field, dark field or transmitted light is used depends on the achievable contrast on the object surface. For example, if the aim during inspection is a resolution of 1 μm in conjunction with the imaging of the object on a semiconductor chip, the system could, for example, be operated at 10 MHz corresponding to 10 megapixels per second.

The invention has been described in detail with particular reference to preferred embodiments thereof and examples, but it will be understood that variations and modifications can be effected within the spirit and scope of the invention.

What is claimed is:

1. A system for inspecting object surfaces, comprising:
    a one dimensionally resolving semiconductor line camera having an objective and having;
    a microscope in the objective, which camera is movable relative to said objective surface,
    a lighting unit, and
    a high resolution positioning system bearing the object to continuously move the object relative to the semiconductor camera at least in terms of two dimensions in order for the semiconductor image at least one image strip.

2. The method as claimed in claim 1, wherein the lighting unit is a changeable lighting unit to vary the lighting characteristics while imaging the object.

3. A method for inspecting object surfaces, comprising:
    positioning an object on a high resolution positioning device;
    focusing a semiconductor line scan camera with one dimensional resolution at a particular point on the position device, through a microscope, the camera having an objective and the microscope being part of the objective of said camera;
    moving the positioning device so as to selectly move different portions of the object into focus for the semiconductor camera; and
    imaging the object while moving the positioning device.

4. The method as claimed in claim 3, wherein image strips are sequentially imaged by the semiconductor camera and evaluated in real time.

5. The method as claimed in claim 3, wherein image strips are sequentially imaged by the semiconductor camera and assembled in an evaluation unit and evaluated subsequently.

6. The method as claimed in claim 3, wherein lighting is performed by transmitting light on the object, in a bright field.

7. The method as claimed in claim 3, wherein lighting is performed by transmitting light on the object, in a dark field.

8. The method as claimed in claim 3, wherein the surface of a semiconductor wafer is inspected.

9. The method as claimed in claim 3, wherein the positioning system is triggered by camera exposure.

10. The method as claimed in claim 3, wherein the object is illuminated using flashes of light.

11. The method as claimed in claim 3, wherein
    the object is illuminated using at least one of transmitted illumination and incident illumination, and
    the incident illumination is executed as dark field or light field illumination.

12. The method as claimed in claim 3, wherein light emitting diodes are used for the transmitted illumination.

13. The method as claimed in claim 3, wherein the positioning device is moved along a meandering path.

14. The method as claimed in claim 3, wherein the positioning device is moved along a rectilinear path.

15. The method as claimed in claim 3, wherein the positioning device is moved along a spiral path.

16. The method as claimed in claim 3, wherein the entire object is imaged while moving the positioning device.

17. The method as claimed in claim 3, further comprising changing the illumination on the object while imaging the object.

18. The method as claimed in claim 8, wherein the positioning system is triggered by camera exposure.

19. The method as claimed in claim 18, wherein the object is illuminated using flashes of light.

20. The method as claimed in claim 19, wherein light emitting diodes are used for illumination.

* * * * *

UNITED STATES PATENT AND TRADEMARK OFFICE
CERTIFICATE OF CORRECTION

| | | |
|---|---|---|
| PATENT NO. | : 6,970,238 B2 | Page 1 of 1 |
| APPLICATION NO. | : 10/258141 | |
| DATED | : November 29, 2005 | |
| INVENTOR(S) | : Detlef Gerhard et al. | |

It is certified that error appears in the above-identified patent and that said Letters Patent is hereby corrected as shown below:

On title page (57); line 4, change "linescan" to -- line scan--

Column 3, line 67, change "having;" to --having--

Column 4, line 2, change "objective" to --object--

Column 4, line 7, after "semiconductor" insert --camera to--

Column 4, line 21, change "selectly" to --selectively--

Signed and Sealed this

Twenty-ninth Day of August, 2006

JON W. DUDAS
*Director of the United States Patent and Trademark Office*